(12) United States Patent
Wallach

(10) Patent No.: US 6,495,368 B1
(45) Date of Patent: Dec. 17, 2002

(54) METHODS AND DEVICES FOR DETECTING MICROBIAL SPOILAGE IN FOOD PRODUCTS

(75) Inventor: Donald F. H. Wallach, Hollis, NH (US)

(73) Assignee: GroupTek, Inc., Andover, MA (US)

( * ) Notice: Subject to any disclaimer, the term of this patent is extended or adjusted under 35 U.S.C. 154(b) by 0 days.

(21) Appl. No.: 08/744,111

(22) Filed: Nov. 5, 1996

(51) Int. Cl.$^7$ .............................................. G01N 33/02
(52) U.S. Cl. ...................... 436/20; 436/163; 436/164; 422/55; 422/61
(58) Field of Search .............................. 436/2, 20, 164, 436/163; 422/55, 61

(56) References Cited

U.S. PATENT DOCUMENTS

| | | | |
|---|---|---|---|
| 4,105,800 A | | 8/1978 | Jahns et al. .................... 426/61 |
| 4,285,697 A | * | 8/1981 | Neary .................... 23/230 LC |
| 4,938,389 A | | 7/1990 | Rossi et al. ................. 222/189 |
| 5,053,339 A | * | 10/1991 | Patel ............................. 436/2 |
| 5,306,466 A | * | 4/1994 | Goldsmith ................... 422/58 |

OTHER PUBLICATIONS

VWR, catalog 1987–1988, p. 776, EM ColorpHast Indicator Strips, 1987.*

Shimoda, Mitsuya et al., "Behavior of diffusion, Permeation and Sorption of Flavor Compounds in Vapor Phase with Polyethylene Film," *Nippon Shokuhin Kogyo Gakkaishi*, vol. 34, No. 6, pp. 402–406 (1987).

Bell, C. et al., "Disposable oxygen electrode system without membranes applied to the detection of ultrahigh–temperature milk spoilage", *Netherlands Milk and Dairy Journal*, vol. 49 pp. 139–149 (1995).

Chang, George et al., "Trimethylamine–specific electrode for fish quality control", *Journal of Food Science*, vol. 41 pp. 723–724 (1976).

Gyosheva, H. et al., "Compounds forming the aroma complex of Bulgarian sour milk", *Milchwissenschaft*, vol. 37, No. 5 pp. 267–269 (1982).

Hajizadeh, K. et al., "Gamma–irradiation immobilization of lactate oxidase in poly (vinyl alcohol) on platinized graphite electrodes", *Analytica Chimica Acta.*, vol. 243 pp. 23–32 (1991).

Hajizadeh, K. et al., "Immobilization of lactate oxidase in a poly (vinyl alcohol) matrix on plantinized graphite electrodes by chemical cross–linking with isocyanate", *Talanta*, vol. 38, No. 1 pp. 37–47 (1991).

Park, Douglas et al., "Rapid Facile Solid–Phase Immunobead Assay for Screening Ciguatoxic Fish in the market place", *Bull. Soc. Path. Ex.*, vol. 85 pp. 504–507 (1992).

* cited by examiner

*Primary Examiner*—Yvonne Eyler
*Assistant Examiner*—E. Lazer-Wesley
(74) *Attorney, Agent, or Firm*—Fish & Richardson PC

(57) ABSTRACT

The present invention pertains to methods and devices for detecting microbial spoilage of a food product. The method involves placing a spoilage indicator device including a barrier sheet in fluid contact with a food product. The method also involves allowing any reactant molecule of a predetermined size produced in the food product by microbial spoilage to traverse the barrier sheet to contact a carrier of the device and to react with an indicator material therein. The method further provides observing the spoilage indicator to determine whether the detectable change has occurred in the indicator material. The detectable change indicates a build-up of the reactant molecule in the food product and therefore is indicative of microbial spoilage.

31 Claims, 2 Drawing Sheets

METHODS AND DEVICES FOR DETECTING MICROBIAL SPOILAGE IN FOOD PRODUCTS

BACKGROUND OF THE INVENTION

The field of this invention concerns the determination of food freshness, and, in particular, methods and devices for the detection of microbial spoilage in food products.

The spoilage and souring of perishable foods with time is an on-going problem for the consumer and food product provider alike. Although some deterioration in freshness is due to oxidative processes, spoilage and souring is in large part due to the growth of microbes such as bacteria, yeasts, and fungi. To derive energy for their growth, these microbes break down food carbohydrates, proteins and fats. The breakdown process produces a variety of low molecular weight molecules such as carboxylic acids (e.g., lactic and acetic acids), aldehydes, nitrogen containing molecules including ammonia, trimethylamine, urea and small diamines, and sulfur compounds. For example, over time, microbes in milk and dairy products produce an increased amount of lactic acid and lactic acid derivatives resulting in sour and odorous milk, respectively. (See, e.g., Gyosheva, B. H., (1982) "Compounds forming the aroma complex of Bulgarian sour milk" *Milchwissenschaft* 37, 267–289).

At present, there are no inexpensive, simple and accurate measurement devices for detecting food spoilage at a consumer level. Spoilage has conventionally been monitored by standard bacteriological and chemical laboratory methods, while certain more esoteric assays have been discussed in the literature to approve speed or cost of detection. For example, electrochemical assays involving gamma-irradiation immobilization of lactate oxidase in poly (vinyl alcohol) on platinized graphite electrodes have been proposed for lactate detection in dairy products (See Hajizadeh, K., et al. (1991) "Immobilization of lactate oxidase in a poly(vinyl alcohol) matrix on plantinized graphite electrodes by chemical cross-linking with isocyanate" *Talanta* 38, 37–47). Other approaches to food spoilage monitoring include, for example, using non-membrane disposable oxygen electrode systems for detection of milk spoilage from aerobic bacteria (See Bell, C. Ackland, et al. (1995) "Disposable oxygen electrode system without membranes applied to the detection of ultrahigh-temperature milk spoilage" *Netherlands Milk and Dairy Journal* 49, 139–149); and modified Orion ammonia electrodes for the trimethylamine detection in fish (See Chang, G. W., et al. (1976) "Trimethylamine-specific electrode for fish quality control" *Journal of Food Science* 41 723–724). However, these techniques are not practical at a consumer level and smell, color or taste has been the major way consumers detect spoilage.

Recently, there have been some attempts at finding a way to help consumers determine whether foods are contaminated by specific toxins. For example, U.S. Patent No. 5,306,466 by Goldsmith discloses packaging with a bar code design formed of labeled antibodies bound to toxins. The bar code design is placed in contact with the juices of a food product, for example by printing it on a membrane in the packaging itself, and a competitive antibody-antigen reaction is used to detect spoilage. The antibodies on the membrane, which react with the specific class of toxins accumulating in the food product's juices, are released from the membrane, thereby destroying the design and providing a visual indication of toxin presence. However, this type of indicator is expensive because of the antibody cost, may not be safe, and has limited applicability.

Similarly, electrode systems, and electrochemical or competitive assay techniques, do not solve the consumer problem. These techniques often involve relatively lengthy or complex procedures, and may have limited applicability. Accordingly, there exists a need for relatively rapid and efficient, accurate, inexpensive and simple methods and devices for indicating microbial spoilage in a variety of food products. Such methods and devices would simplify spoilage indication techniques while maximizing their accuracy, efficacy and applicability through selection of indicators and barriers.

Accordingly, an object of the invention is to provide a method of indicating food spoilage which is simple, accurate and inexpensive.

Another object of the invention is to provide a food spoilage indicator device for placing in fluid contact with a food product.

These and other objects and features of the invention will be apparent from the following description and the drawings.

SUMMARY OF THE INVENTION

The present invention features methods and devices for providing a detectable, e.g., visual, indication of microbial food spoilage. Briefly, a barrier which allows passage of a reactant molecule of a predetermined size but segregates out larger molecules, separates the food product from a carrier which carries an indicator. The indicator provides a detectable change, such as a color change or fluorescence, upon reaction with the reactant molecule. The present invention is also based on the further recognition that such an indicator, carrier and barrier can be placed in a food product package without contaminating the food.

As used herein, the following terms are to be understood in light of the following definitions:

The term "fluid" refers to liquid or gaseous states;

The term "barrier" means a device or portion of a device which provides a physical separation between one location and another or between the device and the product;

The term "reactant molecule" means any molecule produced by microbes in a food product causing spoilage, or a product of a secondary reaction of a molecule produced by the microbes in the food product causing spoilage, which can react with the selected indicator in the device of the invention;

The term "indicator" means any material which can react with the reactant molecule to produce a detectable, e.g., visual change, either through a direct or intermediate reaction;

The term "microbe" means any bacteria, yeast, viruses, fungi, and any similar organism that can cause food spoilage;

The term "spoilage" means any change in a food product making it less palatable or dangerous for consumption by the animal, e.g., human, that would normally eat the food product; and The term "carrier" means any material which entraps or holds an indicator; e.g., paper, other fibrous or cellulosic materials and the like.

The invention concerns a method for detecting microbial spoilage in a food product. A spoilage indicator device is placed in fluid contact with a food product. Reactant molecules produced in the food product by microbial spoilage are allowed to traverse a barrier separating the food product from the carrier in the device and react with the indicator material in the carrier. The detectable change caused by the reaction of the reactant molecule with the indicator indicates a build-up of the reactant molecule in the food product and, therefore, microbial spoilage. The barrier sheet should be permeable to molecules under about 200 daltons but substantially impermeable to larger molecules.

The reactant molecules are produced directly by the microbes or are intermediate by-products related to microbial growth in a food product undergoing spoilage. These reactant molecules exist in liquid and/or gaseous forms and are normally acids, bases, aldehydes, sulfur compounds, or their derivatives, depending upon the type of microbes causing the microbial spoilage. In certain preferred embodiments, the selected barrier will only allow passage of reactant molecules which are in a non-ionized form.

The indicator material is selected based upon the type of food product, the type of suspected microbes, and the type of reactant molecule which is expected to be detected. Preferably, the indicator material produces a visual detectable change, such as a chromatic or fluorescent change, in response to pH or other changes caused by a reaction between the reactant molecules and the indicator materials. Preferred indicator materials are capable of producing detectable changes with pH changes. Preferred pH indicators have a detectable change within the range of about 3.0 to about 8.4. Each individual indicator material produces a detectable change in response to a narrower pH range and the particular indicator used is selected by food type and reactant molecule expected. Preferably, the indicator materials are sensitive enough to produce detectable changes when the reactant molecules are in a concentration of about 0.01% by volume in the fluid surrounding the food product. Additional indicators preferentially react with sulfur containing groups, aldehydes, or nitrogen containing groups such as ammonia, urea or amines. While these materials may cause pH changes as well, sulphydryl or nitrogen compound specific indicators are known in the art. Specific examples of indicator materials involving chromatic changes include, but are not limited to, Bromophenol blue, Bromocresol green, Methyl red, Litmus, Bromocresol purple, Bromothymol blue, Phenol red, Thymol blue, Schiffs base reagent, diphenyl, dinitrophenylhydrazine and sodium nitroferricyanide. Indicator materials involving fluorescent detectable changes include, but are not limited to, Dichlorofluoroscein, Calcein, and Fluorescein.

The choice of carrier and barrier sheet generally depend upon the reactant molecules being detected as well as the chosen indicator material. The carrier must be capable of entrapping the indicator but must allow the reactant molecule access to the indicator. Porous, inert materials are preferred for use as carriers. The carrier generally has a thickness of less than about 1 mm. Preferred carrier materials include, but are not limited to, papers (e.g., untreated cellulose), polyamides, cellulose acetate, gels, foams, glass fibers, plastics, and resins such as an ion-exchange resins. Suitable barrier materials must have the proper molecular weight cut-off properties, be chemically inert, and non-contaminating to the food product. Preferred barrier materials include, but are not limited to, polyethylenes, polyvinyl chlorides or other water resistant or hydrophobic materials. Typically, the barrier sheet has a thickness in a range of about 1 $\mu$m to about 13 $\mu$m.

The spoilage indicator device can also include an outer layer which is transparent, translucent and/or has at least a lucent or transparent portion through which an underlying layer, such as the carrier, can be observed. Such an outer layer can be disposed directly on a second surface of the carrier or on a barrier sheet wrapped around the carrier's first and second surfaces. In some instances, the barrier sheet material can act as the outer layer. Preferred outer layer materials include, but are not limited to, cellulose acetate, vinyl polymers (such as PVC), polyethylene, polypropylene, polystyrene, polycarbonate, polyester thermoplastic, glass or polyamide film.

In a preferred embodiment of the invention, the food spoilage indicator device includes Phenol red A as the indicator entrapped within a paper carrier for detecting an amine produced by spoilage of the food product. In this embodiment, the carrier's first surface is separated from fluid contact with the food product by a barrier such as a food wrap layer, e.g., polyvinyl chloride or polyethylene.

In another preferred embodiment of the invention, the food spoilage indicator device includes a Litmus or a Bromocresol purple indicator material entrapped within a paper carrier for the detection of an acid such as a lactic acid. In this embodiment, the carrier is separated from fluid contact with the food product by a barrier which is acid stable, e.g., hydrophobic layer which allows passage of the reactant molecule while restricting the flow of the liquids of the food product. In a most preferred embodiment, this spoilage indicator device also includes a "window" or a transparent or translucent layer which allows visualization of the indicator from outside the packaging. This window could be a cellulose acetate, glass, polycarbonate, polystyrene or polypropylene outer layer disposed on a second surface of the carrier.

Other features and aspects of the invention will be apparent from the detailed description and the drawing.

DETAILED DESCRIPTION

The present invention pertains to spoilage indicator devices and methods for detecting microbial spoilage of a food product. The spoilage indicator device of the present invention is placed in fluid contact with a food product, and reactant molecules resulting from microbial spoilage traverse a barrier where they react with an indicator. The indicator provides a detectable, preferably visual, indication of the presence of the reactant molecule.

The present invention provides a method of detecting microbial spoilage using the described food spoilage indicator device. The spoilage indicator device has a barrier sheet which is permeable to molecules under about 200 daltons and is substantially impermeable to larger molecules. The spoilage indicator device also includes a carrier having an indicator material entrapped or impregnated therein. The indicator device is placed in fluid contact with a food product and the barrier sheet is disposed in contact with the food product. The indicator material is capable of producing a detectable change upon reacting with a reactant molecule produced in the food product when the food product is undergoing microbial spoilage.

Microbes involved in spoilage of food products are primarily bacteria, yeasts and fungi. For example, aerobic bacteria microbes, such as Salmonella, are involved in the spoilage of a variety of chicken or egg related products such as mayonnaise. Other aerobic bacteria, such as *S. aureus, L. monocyrogenes* and *E. coli* are involved in the spoilage of other products such as milk and ground meat. Anaerobic bacteria, such as *Cl. botulinum* and *Cl. perfringens*, are involved in spoilage of canned goods and other products in anaerobic conditions.

Figure 1:
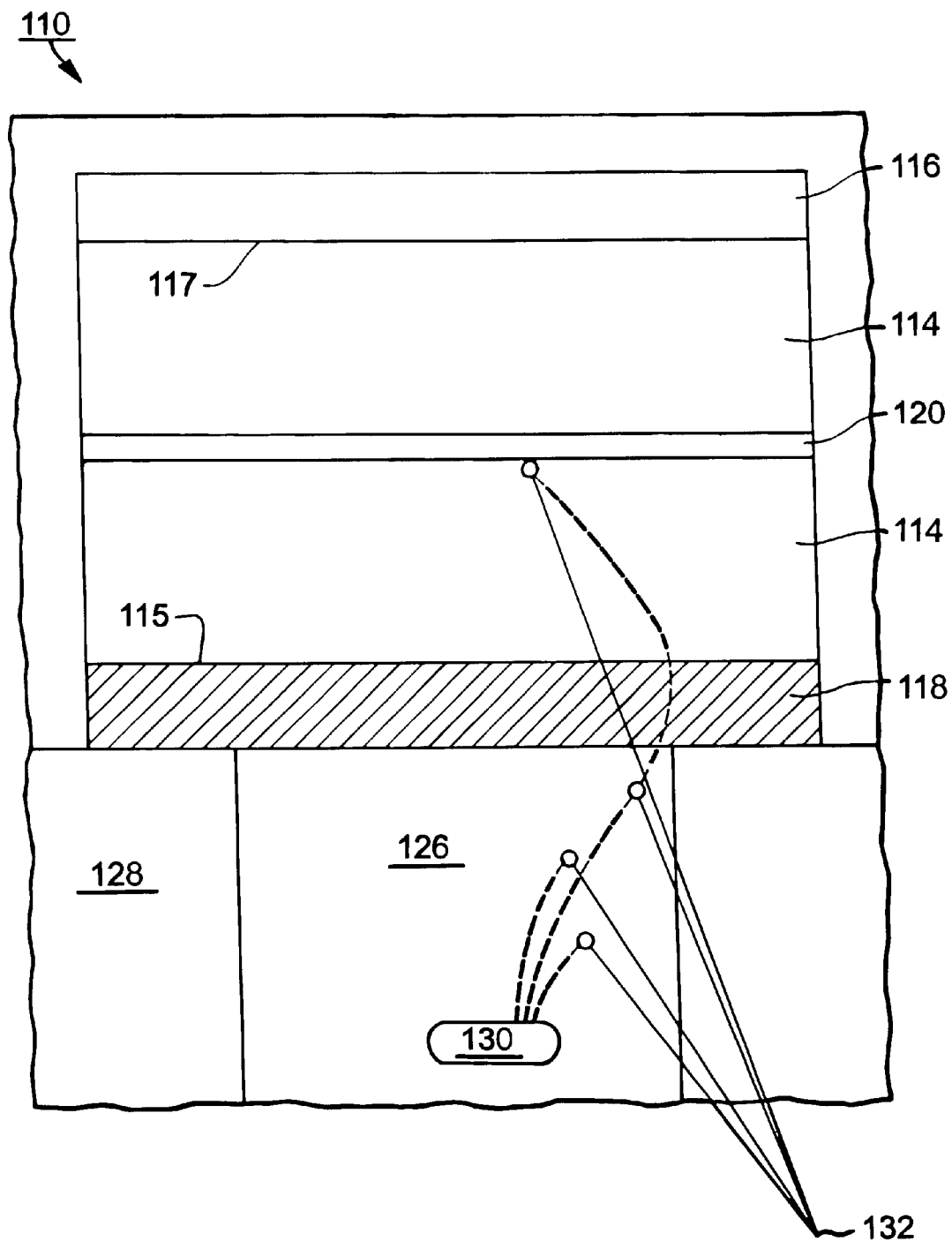
FIG. 1 is an enlarged cut-away side view of the spoilage indicator device, showing a barrier sheet disposed on a first surface of the carrier containing an indicator material.

The following Figures help illustrate the devices and methods of the invention. FIG. 1 shows a cut-away view of an embodiment of the spoilage indicator device 110. Device 110 has a carrier 114 with a first surface 115 directed toward food product 126. Carrier 114 has an indicator material 120 entrapped within it. First surface 115 of carrier 114 is separated from contact with food product 126 and its surrounding juices 128 by a barrier 118. Spoilage indicator device indicator 110 as shown also includes a transparent or translucent outer layer 116 disposed on a second surface 117 of carrier 114. Such an outer layer 116 protects the indicator material 120 entrapped within the carrier 114 from contamination associated with the food packaging.

The barrier layer 118 is disposed directly on the first surface 115 of carrier 114 and may continue beyond the contours of the carrier 114 to form the wrap or food packaging, thereby eliminating additional layers between the carrier 114 and the food. Similarly, outer layer 116 may continue beyond the contours of carrier 114 in the form of a tape or label.

Figure 2:
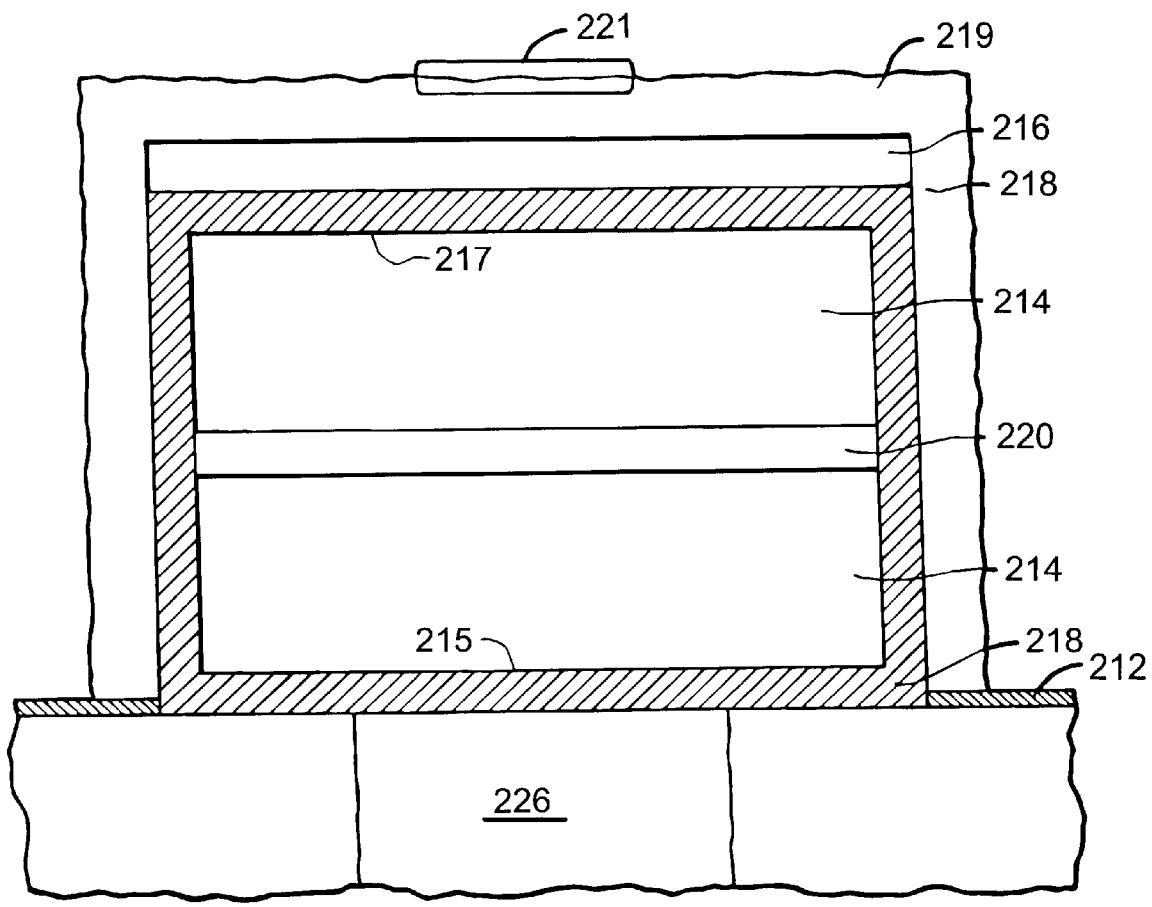
FIG. 2 is a cut-away side view of another embodiment of the spoilage indicator device, wherein the device has a sealed outer surface.

As shown in FIG. 2, the device may have a barrier sheet 218 wrapped around carrier 214, covering both first and second carrier surfaces 215 and 217. Preferably, barrier sheet 218 also extends beyond the contours of the carrier 214 to form a totally sealed package. This type of device is particularly useful if liquids are to be use since it will protect against contamination by splashing.

FIG. 2 further shows the outer layer 216 is sealed with a food-package grade, water- and cold-insensitive tape 219. The tape 219 adheres to the outer layer 216 and to the wrap or food packaging layer 212 if used separately. It is advantageous that tape 219 is provided with a transparent or translucent window 221 to observe the detectable changes of the indicator material 220. Alternatively, tape 219 itself is transparent or sufficiently translucent to allow an observer to view a detectable change in the indicator material 220 through the tape 219.

The spoilage indicator device may be placed in a bottle cap or other part of a liquid containing package without fear of contamination. This device can be placed in direct contact with the food product or volatiles produced by the product can be used to create the detectable change.

In practice, the indicator material, the carrier and the barrier sheet are each selected depending upon the type of food product and microbial spoilage expected, as is readily ascertainable to the skilled artisan. For example, if an amine in an otherwise neutral food product is expected, the food spoilage indicator device may include a paper carrier with a Phenol red A indicator. This combination, with a barrier of a food wrap such as polyvinyl chloride or polyethylene which will pass materials in surround liquids of about 200 daltons or less, can detect amines produced during the microbial spoilage of food products (e.g., meat, fish, shellfish or chicken). Preferably, the barrier is disposed directly on the first surface of the carrier, thereby eliminating an additional food wrap layer.

In a preferred embodiment, a paper carrier with Litmus or a Bromocresol purple indicator material can be used for the detection of lactic acid in milk products. A hydrophobic barrier sheet which passes lactic acid molecules carried as a volatile from the milk separates and protects the carrier from contact with the milk product. This indicator can be used in the cap or as a window in the milk container. If used as a window, an outer layer of a material such as cellulose acetate, glass, polycarbonate, polystyrene or polypropylene is helpful to protect the carrier while providing easy visibility.

In use, the spoilage indicator device of the present invention can be placed such that the indicator is in fluid contact with the food product and/or its surrounding juices. Fluid contact with the food product includes either liquid or gaseous contact, as discussed above, depending upon the application, i.e., the microbial spoilage being detected. With respect to gaseous fluid contact, volatile reactant molecules, once produced, can traverse the barrier sheet to contact the carrier and react with the indicator material. With respect to liquid fluid contact, liquid reactant molecules can traverse the barrier sheet to the carrier. The indicator device can be placed in a variety of ways known to those skilled in the art so long as its placement allows reactant microbial spoilage molecules to contact and to traverse a barrier sheet. The alternatives described above are not intended as limiting the practice of the invention.

Referring again to FIG. 1, during food spoilage, microbes 130, such as bacteria, fungi and yeast grow, derive energy from the break down of food carbohydrates, proteins and fat. The growth of microbes 130 results in the release of reactant molecules 132, either directly as breakdown products or through one or more secondary reactions. Reactant molecules 132 eventually contact and traverse the barrier sheet 118 and react with indicator material 120 to produce a detectable and preferably visual change. Such a detectable change indicates microbial spoilage occurring in the food product 126.

As noted, each indicator material is selected based upon the particular microbial spoilage process being monitored and the associated predetermined reactant molecules resulting from such spoilage. For example, to detect aldehydes, an indicator material such as Schiffs base reagent may be used. Since pH indicators are well known and generally inexpensive, pH is an easy test to use. Examples of some pH sensitive indicator materials, as well as the pH ranges at which they change from first to second colors, are shown in Table 1.

TABLE 1

| Indicator Material | First color | Second Color | ≧pH Range at which indicator material changes from first to second colors |
| --- | --- | --- | --- |
| Bromophenol blue | yellow | purple | 3.0–4.6 |
| Bromocresol green | yellow | blue | 3.8–5.4 |
| Methyl red | red | yellow | 4.8–6.0 |
| Litmus | red | blue | 5.0–8.0 |
| Bromocresol purple | yellow | violet | 5.2–6.8 |
| Bromothymol blue | yellow | blue | 6.0–7.6 |
| Phenol red | yellow | red | 6.8–8.4 |

Other selected indicator materials exhibit fluorescence when contacted with a fluid having a predetermined pH range. Examples of fluorescent indicator materials, as well as the pH ranges at which they fluoresce, are shown in Table 2.

TABLE 2

| Fluorescent Indicator Material | <4.0–5.0 pH Range | >4.0–5.0 pH Range |
|---|---|---|
| Dichlorofluorescein | no fluorescence | green fluorescence |
| Calcein | no fluorescence | green fluorescence |
| Fluorescein | no fluorescence | green fluorescence |

Reactant molecules produced by food products undergoing microbial spoilage include acids, bases, aldehydes, sulfur compounds, and their derivatives. The barrier is selected to pass the desired reactant while retaining the indicator and excluding larger, unwanted molecules. Some barriers only pass selected reactant molecules in their non-ionized form so these barrier can be used with only certain food/microbe combinations. For example, as described infra in example 1, a barrier of polyvinyl chloride preferentially passes the non-ionized form of lactic acid. Particular examples of reactant molecules resulting from microbial spoilage include carboxylic acids, such as acetic or lactic acids; acid derivatives such as acetylaldehydes, basic molecules containing nitrogen such as ammonia, urea, and amines (e.g., trimethylamine and small diamines having a molecular weight of less than about 200 daltons) and sulfur containing molecules such as hydrogen disulfide.

Various carriers for entrapping an indictor material are known to those of ordinary skill in the art. Examples of such carriers include paper (e.g., untreated cellulose), polyamides, cellulose acetate, gels, foams, glass fibers and resins such as ion-exchange resins. The carrier is selected depending upon the type of microbial spoilage and the food. For example, untreated cellulose includes free aldehyde groups so this carrier would not be suitable for the detection of aldehyde reactant molecules. Instead, a carrier formed of cellulose acetate, glass fiber, gelatin, polyacrylic gels or other type of plastics which do not contain free aldehyde groups would be preferred for aldehyde detection. The carriers of the present invention generally have thickness of less than about 1 mm.

A variety of barrier sheets which can be used for separating the carrier from fluid contact with the food product are also known in the art. These include various hydrophobic materials, low- or medium- density polyvinyl chlorides, polyethylenes, and other plastics with extractable hexane and monomer levels meeting Food and Drug Administration standards for food wrappings. The barrier sheets preferably have thicknesses in the range of about 1 $\mu$m to about 13 $\mu$m.

The exemplary indicator materials, carriers, barrier sheets and outer layers discussed above are presented for illustrative purposes only and are not intended to limit the invention.

The following non-limiting Examples further illustrate the efficacy of the invention. In each of Examples 1, 2 and 3, aqueous "donor" compartments containing several concentrations of acidic or basic metabolite were separated by a barrier from aqueous "receptor" compartments containing the indicator material. Changes in indicator color were monitored in triplicate as a function of time and acid concentration.

EXAMPLE 1

This Example was designed to show that acids which can be produced in microbial spoilage can trigger visual effects in a spoilage indicator as described herein. Permeation of lactic and acetic acids at different molar concentrations through separating films consisting of food packaging-grade "cling-wrap" polyvinyl chloride films was tested over a 48 hour period. These films were of the type used and sold by supermarkets and had a thickness of 11.4 microns. The Bromocresol purple concentration was 0.001%. The Bromocresol purple is purple at pH 6.8 and yellow at pH 5.2.

The results of these experiments are shown in the Table 3. The color code of Table 3 is as follows: Gr=gray; P=purple; and Y=yellow. Significant change of color is indicated in bold.

TABLE 3

| | Time | | | | | | |
|---|---|---|---|---|---|---|---|
| Color at | 0 | 2 h | 4 h | 8 h | 24 h | 48 h | pH$_{48 h}$ |
| Lactic acid (M) | | | | | | | |
| 0.01 | P | P | P | P | P | GrP | 6.1 |
| 0.03 | P | P | P | P | GrP | Y | 5.1 |
| 0.05 | P | P | P | PGr | PY | Y | 4.4 |
| 0.1 | P | P | GrP | GrY | Y | Y | 4.0 |
| 0.2 | P | YP | GrPY | Y | Y | Y | 3.6 |
| Acetic acid (M) | | | | | | | |
| 0.01 | P | GrP | GrPY | Y | Y | Y | 4.1 |
| 0.05 | P | PY | Y | Y | Y | Y | 3.7 |
| 0.1 | P | Y | Y | Y | Y | Y | 3.4 |

The data provided clear evidence of permeation, as indicated by indicator color change, a concentration dependence of permeation rate and more rapid permeation of the smaller molecule, acetic acid, as compared with lactic acid.

EXAMPLE 2

The experiment described in Example 1 was repeated except for using a Bromocresol green (0.001%) as the indicator material. The results of this experiment are shown in the Table 4. The indicator is blue at pH 5.2, and yellow at pH 3.6. The color code of Table 4 is as follows: B=blue; G=green; T=turquoise; and Y=yellow. Significant change of color is indicated in bold.

TABLE 4

| | Time | | | | | | |
|---|---|---|---|---|---|---|---|
| Color at | 0 | 2 h | 4 h | 8 h | 24 h | 48 h | pH$_{48 h}$ |
| Lactic acid (M) | | | | | | | |
| 0.01 | B | T | T | T | T | T | 4.8 |
| 0.03 | B | T | T | T | T | Lime | 4.5 |
| 0.05 | B | T | T | T | BG | BYG | 4.0 |
| 0.1 | B | BT | BT | BYG | Lime | Y | 4.0 |
| 0.2 | B | BT | BT | BYG | GY | Y | 4.0 |
| Acetic acid (M) | | | | | | | |
| 0.01 | B | T | TG | TG | BY | Y | 4.1 |
| 0.05 | B | TGY | PG | GY | Y | Y | 3.6 |
| 0.1 | B | YG | GY | Y | Y | Y | 4.0 |

Bromocresol purple appeared to provide a higher sensitivity than Bromocresol green for the test system and pH range utilized.

EXAMPLE 3

In this Example, permeation of acetic and lactic acids (0.1 M) through separating films consisting of food packaging-grade "cling-wrap" polyethylene with thicknesses of 12.7 $\mu$m was tested over a 48 hour time period. Three different indicator materials, Bromophenol blue (0.001%), Bromocresol green (0.001%), and Bromocresol purple (0.001%), were selected for testing. The results are shown in the Table 5. The color code of Table 5 is as follows: B=blue; G=green; Gr=gray; P=purple; T=turquoise; Y=yellow. Significant change of color is indicated in bold.

TABLE 5

| | Time | | | | | | |
|---|---|---|---|---|---|---|---|
| Color at | 0 | 2 h | 4 h | 8 h | 24 h | 48 h | $pH_{48\,h}$ |
| Lactic acid (0.1 M) | | | | | | | |
| Bromophenol blue (0.001%) | B | B | B | B | B | B | 3.5 |
| Bromocresol green (0.001%) | TB | TB | TB | TB | TB | Y | 3.4 |
| Bromocresol purple (0.001%) | P | P | P | Y | Y | Y | 3.1 |
| Acetic acid (0.1M) | | | | | | | |
| Bromophenol blue (0.001%) | B | B | B | B | GrB | GRB | 4.2 |
| Bromocresol green (0.001%) | TB | TB | T | GT | YG | YG | 4.2 |
| Bromocresol purple (0.001%) | P | P | PGr | Y | Y | Y | 4.3 |

Bromocresol purple appeared to be the most effective indicator tested under these conditions. Bromophenol blue did not appear very effective because of its low pH range of sensitivity.

EXAMPLE 4

In this Example, different papers were tested to see which worked better as carriers for different indicators. One of the papers tested, onion skin paper, gave sharp spots, but it was too thick and opaque for use. In contrast, cigarette wrapping paper or white tissue paper were preferable to onion skin paper because they were substantially thinner and the color change occurred on both sides almost simultaneously.

EXAMPLE 5

In this Example, permeation of trimethylamine through polyvinyl chloride film, using Phenol red as indicator, was tested over a 24 hour period. In this and the following Examples, the reactant molecules are volatile, permeating through the gas phase. The polyvinyl chloride film was of a food packaging, cling-wrap type. Two (2) $\mu l$ of 0.01% Phenol red in ethanol was applied onto cigarette wrapper paper and air-dried, yielding a 5–10 $mm^2$, pale-yellow spot. The paper was covered by polyvinyl chloride film, forming a sandwich. The sandwich was stretched across the internal surface of the polyethylene stoppers of a Fisher 0333927F vial with the paper toward the stopper and the stopper inserted into a vial containing 15 ml trimethylamine in water. Phenol red is purplish red at pH 8.4 and yellow at pH 6.8. Color was monitored visually through the bottom of the vial at stated times. The impregnated papers were dry at the end of the experiments. The results are shown below in Table 6. The color code of Table 6 is as follows: R=red; and Y=pale yellow.

TABLE 6

| | Time | | | | | |
|---|---|---|---|---|---|---|
| Color at | 0 | 5 min | 1 h | 8 h | 16 h | 24 h |
| Trimethylamine (%; v/v) At room temperature | | | | | | |
| 0.001 | Y | Y | Y | YR | R | R |
| 0.0025 | Y | Y | Y | YR | R | R |
| 0.01 | Y | Y | YR | R | R | R |
| 0.1 | Y | R | R | R | R | R |
| At 10° C. | | | | | | |
| 0.001 | Y | | Y | YR | R | |
| 0.0025 | Y | | Y | YR | R | |
| 0.01 | Y | | Y | R | R | |
| 0.1 | Y | | R | R | R | |

Screening experiments performed with ammonium hydroxide solutions indicated faster reaction times than trimethylamine; an expected result since the molecular weight of ammonia is 0.29 that of trimethylamine.

EXAMPLE 6

In this Example, permeation of trimethylamine through polyvinyl chloride film using Bromothymol blue as indicator was tested over a 24 hour period. The polyvinyl chloride film was of the food packaging cling-wrap type. Two (2) $\mu l$ of 0.01% Bromothymol blue in ethanol was applied onto cigarette wrapper paper and air-dried. As in Example 5, the paper was covered by PVC film forming a sandwich and the sandwich is stretched across the internal surface of the polyethylene stoppers of a Fisher 0333927F vial with the paper toward the stopper and the stopper inserted into a vial containing 15 ml trimethylamine in water.

The results of the experiment are provided in Table 7. Bromothymol blue is blue at pH 7.6 and yellow at pH 6.0. Color was monitored visually through the bottom of the vial at stated times. The impregnated papers were dry at the end of the experiments.

The color code of Table 7 is as follows: B=blue, G=green, Y=yellow.

TABLE 7

| | Time | | | | | |
|---|---|---|---|---|---|---|
| Color at | 0 | 5 min | 1 h | 8 h | 16 h | 24 h |
| Trimethylamine (%; v/v) At room temperature | | | | | | |
| 0.01 | Y | Y | G | GB | GB | B |
| 0.1 | Y | B | B | B | B | B |
| 0.4 | Y | B | BR | B | B | B |

As is clearly indicated by the Examples, the present invention provides methods and devices for detecting microbial spoilage in a variety of food products. Because of the simplicity, efficiency, accuracy and wide applicability of the spoilage indicator methods and devices described herein, the present invention presents numerous advantages over the prior art.

The invention is not limited by the specific description herein but its scope is governed by the following claims.

What is claimed is:

1. A method of detecting microbial spoilage of a food product comprising the steps of:

placing a spoilage indicator device in fluid contact with a food product, said spoilage indicator having a barrier sheet which is permeable to molecules under about 200 daltons while being substantially impermeable to larger molecules, said spoilage indicator further containing a carrier having an indicator material entrapped therein, said indicator material being selected from the group consisting of pH sensitive indicators, sulphydryl and nitrogen compound specific indicators said barrier sheet being arranged so that it is in fluid contact with said food product and separating a first surface of said carrier from said food product, said indicator material being capable of producing a detectable change upon reacting with a reactant molecule of less than 200 daltons which is produced in a food product when the food product is undergoing microbial spoilage;

allowing a reactant molecule produced in said food product by microbial spoilage to traverse said barrier sheet, to contact said spoilage indicator, and to react with said indicator material therein; and observing said spoilage indicator to determine whether said detectable change has occurred in said indicator material, said detectable change indicating a build-up of said reactant molecule in said food product and therefore being indicative of microbial spoilage.

2. The method of claim 1, further comprising the step of providing the indicator material being capable of producing the detectable change upon reacting with the reactant molecule, wherein the reactant molecule is in a liquid phase.

3. The method of claim 1, further comprising the step of providing the indicator material being capable of producing the detectable change upon reacting with the reactant molecule, wherein the reactant molecule is volatile.

4. The method of claim 1, further comprising the step of providing the indicator material being capable of producing the detectable change upon reacting with the reactant molecule, wherein the reactant molecule is an acid.

5. The method of claim 1, further comprising the step of providing the indicator material being capable of producing the detectable change upon reacting with the reactant molecule, wherein the reactant molecule is a base.

6. The method of claim 1, further comprising the step of providing the indicator material being capable of producing the detectable change upon reacting with the reactant molecule, wherein the reactant molecule is in a non-ionized form.

7. The method of claim 1, further comprising the step of providing the indicator material being capable of producing the detectable change upon reacting with the reactant molecule, wherein the reactant molecule includes nitrogen.

8. The method of claim 1, further comprising the step of providing the indicator material being capable of producing the detectable change upon reacting with the reactant molecule, wherein the reactant molecule includes sulfur.

9. The method of claim 1, further comprising the step of providing the indicator material being capable of producing a visual detectable change.

10. The method of claim 9, wherein the visual detectable change is a chromatic detectable change.

11. The method of claim 10, wherein the step of providing the indicator material comprises selecting the indicator material from the group consisting of Bromophenol blue, Bromocresol green, Methyl red, Litmus, Bromocresol purple, Thymol blue, Phenol red, Schiff's base reagent, diphenyl, dinitrophenylhydrazine and sodium nitroferricyanide.

12. The method of claim 9, wherein the visual detectable change is a fluorescent detectable change.

13. The method of claim 12, wherein the step of providing the indicator material comprises selecting the indicator material from the group consisting of Dichlorofluoroscein, Calcein, and Fluorescein.

14. The method of claim 1, further comprising the step of providing the carrier having a thickness of less than about 1 mm.

15. The method of claim 7, wherein the step of providing the carrier comprises selecting the carrier from the group consisting of paper, polyamide, cellulose acetate, gel, foam, glass fiber and resin.

16. The method of claim 1, further comprising providing the barrier sheet having a thickness in a range of about 1 $\mu$m to about 13 $\mu$m.

17. The method of claim 16, wherein the step of providing the barrier sheet comprises forming the barrier sheet from a hydrophobic layer.

18. The method of claim 1, further comprising the step of providing an outer layer disposed on a second surface of the carrier.

19. The method of claim 11, wherein the step of providing the outer layer comprises selecting the outer layer from the group consisting of cellulose acetate, polyethylene, polypropylene, polystyrene, polyvinyl chloride, polycarbonate, polyester thermoplastic, glass and polyamide film.

20. A spoilage indicator device for placing in fluid contact with a food product to detect microbial spoilage, said spoilage indicator device having a barrier sheet which is permeable to molecules under about 200 daltons while being substantially impermeable to larger molecules, said barrier sheet being arranged so in use it is in fluid contact with said food product, said spoilage indicator device further containing a carrier having an indicator material entrapped therein, said indicator material being selected from the group consisting of pH sensitive indicators, sulphydryl and nitrogen compound specific indicators, said barrier sheet separating a first surface of said carrier from said food product, said indicator material being capable of producing a detectable change upon reacting with a reactant molecule of less than 200 daltons which is produced in said food product when said food product is undergoing microbial spoilage and traverses said barrier sheet.

21. The device of claim 20, wherein the detectable change is a visual change.

22. The device of claim 21, wherein the visual change is a chromatic change.

23. The device of claim 21, wherein the visual change is a fluorescent change.

24. The device of claim 20, wherein the carrier is a paper.

25. The device of claim 20, wherein the carrier has a thickness of less than 0.1 mm.

26. The device of claim 20, wherein the barrier sheet is a hydrophobic layer.

27. The device of claim 20, wherein the barrier sheet is selected from the group consisting of polyethylene and polyvinyl chloride.

28. The device of claim 20, wherein the barrier sheet has a thickness in a range of about 1 $\mu$m to about 13 $\mu$m.

29. The device of claim 20, further comprising:

an outer layer disposed on a second surface of the carrier.

30. The device of claim 20, wherein the outer layer comprises a polyamide film.

31. The device of claim 21, wherein the outer layer is selected from the group consisting of cellulose acetate, glass, polycarbonate, polystyrene and polypropylene.

* * * * *